United States Patent [19]

Watts et al.

[11] Patent Number: 5,336,998

[45] Date of Patent: Aug. 9, 1994

[54] SENSOR FOR DETECTING FAULTS IN A MAGNETIZED FERROUS OBJECT USING HALL EFFECT ELEMENTS

[75] Inventors: Kenneth J. Watts; Stephen A. Ingram, both of Birmingham, Ala.

[73] Assignee: United States Pipe and Foundry Company, Birmingham, Ala.

[21] Appl. No.: 902,207

[22] Filed: Jun. 22, 1992

[51] Int. Cl.⁵ .................... G01N 27/83; G01R 33/06
[52] U.S. Cl. .................... 324/235; 324/242; 324/251
[58] Field of Search ............... 324/235, 237, 239, 240, 324/242, 241, 243, 207.20, 262

[56] References Cited

U.S. PATENT DOCUMENTS

| | | |
|---|---|---|
| 1,998,952 | 4/1935 | Edgar et al. |
| 2,260,589 | 10/1941 | Smith |
| 2,543,640 | 2/1951 | Millar et al. |
| 2,562,120 | 7/1951 | Pearson |
| 2,649,569 | 8/1953 | Pearson |
| 2,736,822 | 2/1956 | Dunlap, Jr. |
| 2,740,090 | 3/1956 | Dionne |
| 2,798,989 | 7/1957 | Welker |
| 2,942,177 | 6/1960 | Neumann et al. |
| 2,946,955 | 7/1960 | Kuhrt |
| 3,484,682 | 12/1969 | Wood |
| 3,579,099 | 5/1971 | Kanbayashi |
| 3,816,766 | 6/1974 | Anselmo et al. ................. 307/278 |
| 4,538,108 | 8/1985 | Huschelrath ...................... 324/232 |
| 4,763,070 | 8/1988 | Huschelrath ...................... 324/225 |
| 4,970,463 | 11/1990 | Wolf et al. ..................... 324/235 X |
| 5,105,151 | 4/1992 | Takahashi et al. ................ 324/235 |
| 5,128,613 | 7/1992 | Takahashi ........................ 324/235 |

Primary Examiner—Gerard R. Strecker
Assistant Examiner—Warren S. Edmonds
Attorney, Agent, or Firm—James W. Grace

[57] ABSTRACT

A sensor for detecting faults in a magnetized ferrous body which has a first ferrite disc having at least two opposed sides, a pair of Hall Effect semiconductors, the Hall Effect semiconductors being affixed to opposite sides of said ferrite disc and a pair of ferrite discs, each ferrite disc of said pair of ferrite discs being affixed to a side of each of said Hall Effect semiconductors opposite the side of said Hall Effect semiconductors which is affixed to the first ferrite disc.

11 Claims, 2 Drawing Sheets

SENSOR FOR DETECTING FAULTS IN A MAGNETIZED FERROUS OBJECT USING HALL EFFECT ELEMENTS

BACKGROUND OF THE INVENTION

1. Field of the Invention

This invention relates to a sensor to detect faults in a ferrous object and, more particularly, to a sensor to detect magnetic flux leakage from a discontinuity in a magnetized object. The invention will be described in relation to the detection of a crack in a ferrous pipe, although the invention is broader in scope.

2. Description of the Prior Art

In the prior art there are numerous systems for detecting faults or cracks in ferrous objects and more particularly ferrous pipes.

One accepted method of inspection for faults is by an ultrasonic fault detector. There are many brands and types of ultrasonic fault detectors on the market. The ultrasonic transducer requires a couplant, such as, water or glycerine, to conduct the ultrasound wave into the metal and return the echo. Thus, a full length scan of a pipe around 360 degrees of circumference by the ultrasonic method is both slow and. messy. The echo signal that is returned by ultrasonic examination of a cylindrical object, a pipe, is made complex by the multiple reflections from the inside and outside walls. Considerable experience is required to interpret the signal data to confirm the existence of a fault. Background ultrasonic noise, generated by plant equipment, masks the signal generated by the fault.

Another method of fault detection is monitoring magnetic flux leakage. A fault in a ferromagnetic material may be detected if that material has been magnetized and the fault causes a discontinuity in the path through which the magnetic field travels. The fault causes a perturbation in the magnetic field around the test piece. Two devices are used to detect perturbations in a magnetic field, a coil of wire and a Hall Effect semiconductor. Both detectors provide rapid detection of a fault. The output voltage which the coil of wire produces is dependent on the strength of the magnetic field and the velocity with which the coil passes through the field. The output of the Hall Effect semiconductor device depends only on the strength of the field. The Hall Effect sensor produces an output voltage proportional to the magnetic field in which it rests even if the sensor is mechanically static. However, the Hall Effect semiconductor may not function well if the magnetic field is not strong enough.

Another system of fault detectors uses magnetic field pattern detectors or sensors arranged near the surface of the ferrous bodies but the outputs of the sensors are connected in a specific sequence and in a time-division multiplex manner to an evaluation circuit. Such a fault detector is disclosed in U.S. Pat. No. 4,763,070 but the circuit is of such complexity as not to be of commercial value. An earlier version of this type detection system may be found in U.S. Pat. No. 4,538,108.

The use of a Hall cell to detect faults is described in U.S. Pat. No. 3,816,766. This patent concerns mainly the problem of temperature sensitivity of the Hall Circuit. In this type of Hall detector, the magnetic field may not be strong enough to cause the detector alone to be useful under production conditions requiring rapid and accurate responses.

SUMMARY OF THE INVENTION

The present invention is directed to a fault detector sensor in which a Hall Effect semiconductor detects the magnetic flux of a remanent magnetic field of a ferrous object, which magnetic flux has been enhanced by adjacently spaced ferrite discs having high magnetic permeability.

OBJECTS OF THE INVENTION

It is an object of the invention to provide a fault detector sensor for ferrous objects which fault detector sensor is very accurate.

It is a further object of the invention to provide a fault detector which will not disrupt the conventional production process for ductile iron pipe.

BRIEF DESCRIPTION OF THE DRAWINGS

The foregoing and other objects, advantages and features of the invention will become apparent to those skilled in the art from a consideration of the following detailed description of the invention taken in conjunction with the accompanying drawings in which like elements are represented by like numerals and in which.

DESCRIPTION OF THE PREFERRED EMBODIMENT

Figure 1:
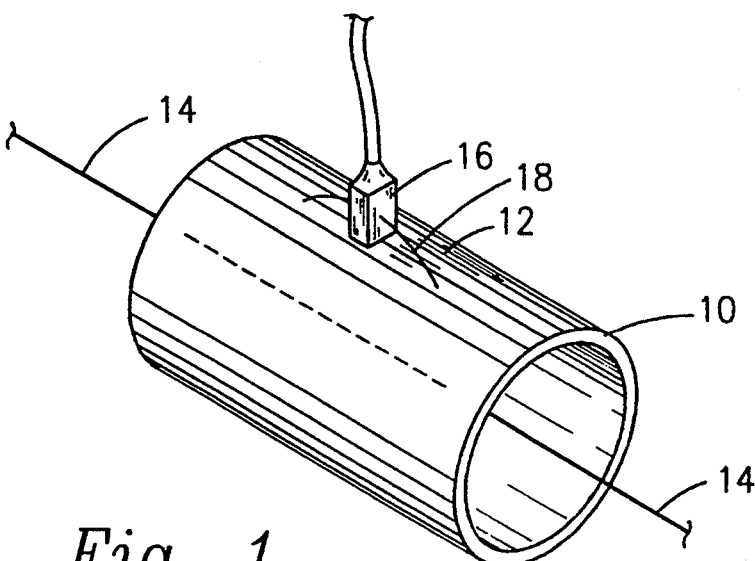
FIG. 1 is a perspective view of a Hall Effect semiconductor shown in relation to the surface of a ductile iron pipe.

Referring now to FIG. 1, there is shown a section of ductile iron pipe 10 having a fault or crack 12 in a portion of the wall thereof. Ductile iron pipe 10 may be made by the well-known centrifugal casting process of using molten iron as the ferrous material. The process for making a centrifugal cast ductile iron pipe may be found in U.S. Pat. No. 3,415,307, entitled: "Process for casting Ductile Iron" and assigned to United States Pipe and Foundry Company.

The pipe is magnetized by a wire 14 that passes through approximately the center of the pipe from bell end to spigot end. A direct current of approximately 8000 amperes for a duration of approximately 5 milliseconds is applied to the wire. A magnetic field is created in the pipe wall by the passage of this current through the wire. After the current goes to zero and the wire is removed, a magnetic field will remain in the pipe wall. This field is called the remanent field. Its strength will be less than the current-on field and is determined in part by the magnetic permeability of the ferrous material.

Once the pipe is magnetized, it can be transported to another station for detection of faults by the sensors.

The magnetic field in the pipe wall will last, theoretically, forever. A row of sensors placed above the pipe will detect faults as the pipe is rotated. Approximately 64 of these sensors will cover the pipe from bell to spigot and one rotation of the pipe will cover the entire outside surface.

A Hall Effect semiconductor 16 is shown in position above fault 12 with its sensitive surface perpendicular to the surface of the pipe. The magnetic flux 18 that leaves the pipe through fault 12 will penetrate the Hall Effect semiconductor causing maximum voltage output. The magnetic flux 18 that leaks from the pipe wall forms a loop through the air across the fault. The sensitivity of the Hall Effect semiconductor may be high enough to sense and locate a large fault if the semiconductor is placed on the pipe with no gap. However, for the semiconductor to be of practical value in the manufacturing process, a gap was found to be necessary between the Hall Effect 16 semiconductor and the pipe 10.

For a more detailed description of a Hall Effect semiconductor reference may be had to U.S. Pat. No. 2,942,177, entitled: "Method and Means for Measuring Magnetic Field Strength," issued Jun. 21, 1960, the teachings of which are incorporated herein by reference.

The solution to the sensitivity problem is what makes the fault detector sensor of the invention unique. The volume of space above both sensitive surfaces of the Hall Effect semiconductor 16 is filled with a material whose magnetic permeability is much greater than air. This higher magnetic permeability region tends to concentrate the magnetic flux on either side of the Hall Effect semiconductor 16. The flux through the Hall Effect semiconductor 16 is increased because it is located between these two regions. The proximity of the semiconductor to the high permeability material increases the sensitivity of the combination above the sensitivity of the semiconductor 16 alone. The material that is used as the flux concentrator is sintered ferrite. This material is a powder that is compression molded into the desired shape and sintered in an oven. The ferrite discs in the sensor are manufactured by D. M. Steward Manufacturing Company in Chattanooga, Tenn. The material is a sintered ferrite powder with magnetic permeability of 850. This means that it will hold about 850 times more magnetic lines of force than air.

Figure 2:
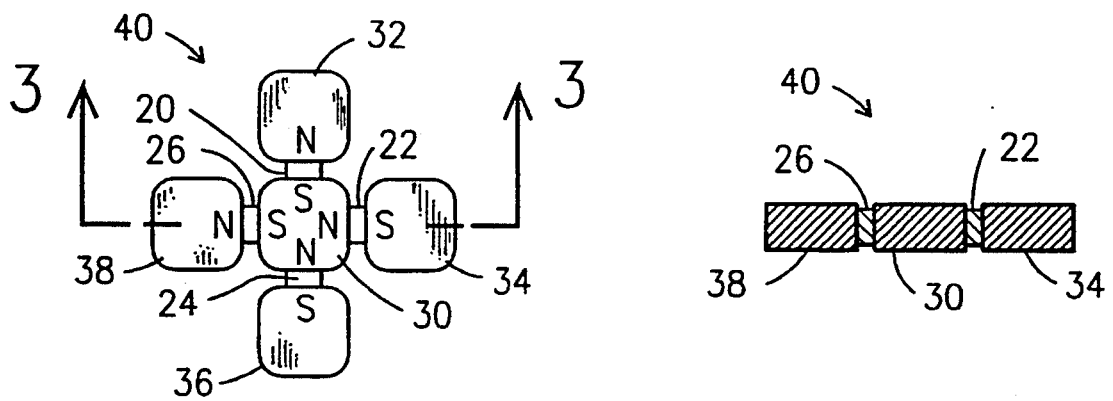
FIG. 2 is a top view of the fault detector sensor of the invention.

As shown in FIG. 2, four individual Hall Effect semiconductors 20, 22, 24, and 26 are combined with five ferrite discs 30, 32, 34, 36, and 38 in an array that forms the crack detector sensor 40. This array, when attached to the proper electronic circuitry, displays a unique electronic signature after a magnetic perturbation, such as a crack, crosses the sensitive plane of the array.

The fault detector sensor array 40 is constructed by attaching four Hall Effect semiconductors to five of the ferrite discs. Each of the ferrite discs 30-38 is generally quadrilateral in configuration. At the center of the fault detector sensor array 40 is ferrite disc 30. Attached to separate sides of ferrite disc 30 are Hall Effect semiconductors 20, 22, 24, and 26. One semiconductor is attached to each of the four sides of ferrite disc 30.

Attached to each of the semiconductors 20, 22, 24, and 26 is a ferrite disc 32, 34, 36, and 38 respectively, so that the array has three ferrite discs and two Hall Effect semiconductors in a first row at right angles to a second row which has three ferrite discs and two Hall Effect semiconductors. Each row forms an element of the array, as will be discussed hereinafter.

Figure 3:
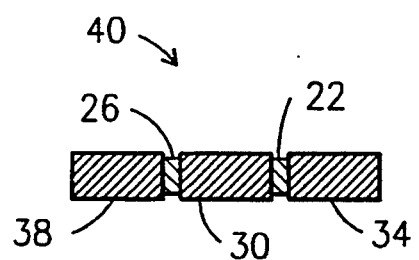
FIG. 3 is a cross-sectional view of the fault detector sensor of the invention taken along line 3—3 of FIG. 2.

FIG. 3 shows a side elevational view of the semiconductor array shown in FIG. 2. The active surface of each semiconductor is in the same plane, with respect to the pipe wall, as in FIG. 1. The north/south directivity of the semiconductor is important. Each semiconductor must be oriented as shown in FIG. 2 so that the electronic detector can process the signal from the array. The orientation of the semiconductor in the array with respect to its flux polarity is important because the output signal from the operational amplifier will be in a positive direction when the crack crosses one semiconductor in the pair and in a negative direction when the crack crosses the other semiconductor. Semiconductors 20 and 24 in FIG. 2 form a pair. The voltage output signals from this pair are subtracted from each other in an electronic circuit. As long as both semiconductors detect the equal magnitudes of magnetic flux, then the voltage output from the electronic circuit is zero.

Figure 4:
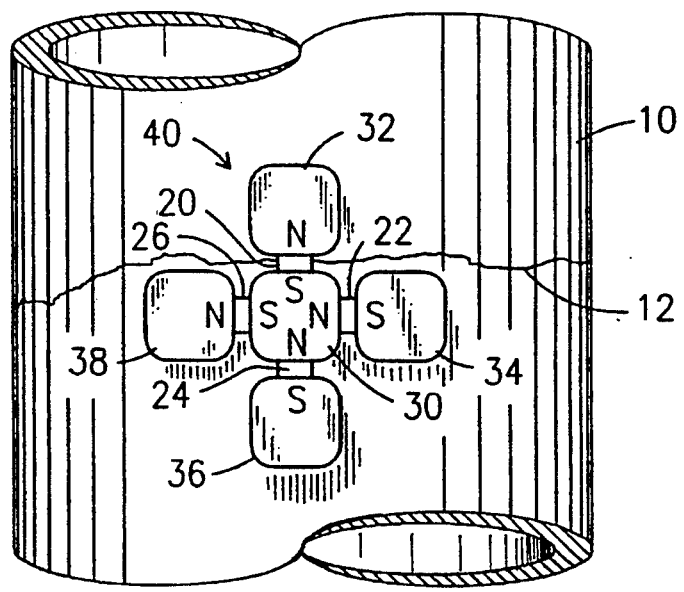
FIG. 4 is a top view of the fault detector sensor of the invention in an operative position.

When a crack 12 in a pipe wall 10 is positioned under one of the semiconductors 20 (FIG. 4), the semiconductor 20 detects a higher magnetic flux due to the flux leakage around the crack. The voltage output of this semiconductor 20 is higher than the other semiconductor 24 in the pair. The voltage output from the electronic subtraction circuit is no longer zero. The presence of the non-zero signal indicates that a crack exists in the pipe wall.

The effect of using the ferrite discs is to make the sensor more sensitive to magnetic fields near it. The Hall Effect semiconductor is also sensitive to magnetic flux polarity. The magnitude of the current output of the semiconductor is dependent on the direction of magnetic flux polarity on the face of the chip. Taking advantage of this feature, the sensor is oriented so that opposite semiconductors face the same direction in the array. Thus, semiconductors 20 and 24 face the same way, as do semiconductors 22 and 26. In FIG. 2, ferrite discs 32, 30, and 36 along with semiconductors 20 and 24 form a first sensing element of the array 40. Ferrite discs 34, 30 and 38 along with semiconductors 22 and 26 form a second sensing element of the array 40. The north and south polarity of each semiconductor is indicated. The first sensing element will detect cracks in one direction, for example, the longitudinal direction, while the sensing element composed of ferrite discs 38, 30, and 34 and semiconductors 26 and 22 will detect cracks in the circumferential direction.

When the sensor passes over a crack (See FIG. 4), the crack enters the region formed by the detector, comprising ferrite discs 32 and 30 along with semiconductor 20. The magnetic flux leaves one side of the crack, goes through ferrite disc 32, semiconductor 20 and ferrite disc 30 then back into the other side of the crack. The semiconductor 20 will emit a current that is proportional to the magnitude of the magnetic flux. As the sensor proceeds over the crack, a similar signal is emitted by the detector formed by ferrite discs 30 and 36 with semiconductor 24. The two signals go to the electronic circuit shown in FIG. 5. If an electromagnetic pulse is received by both detectors simultaneously, i.e., having its origin outside the boundary of the sensor and hence not from a crack, the electronics will null the signals so that they will not cause the instrument to give a spurious indication of a crack. Each sensing element of the sensor has a separate subtraction circuit. Cracks that run at angles to the sensor other than 90 degrees will be detected. The output of the semiconductor will be proportionately less as the angle deviates from 90 degrees. Cracks that run 90 degrees to the axis of an element will be detected with the greatest amplitude of output. Cracks that are parallel with an element will not be detected. Any crack that runs at an angle between 0 and 90 degrees will be detected by both elements of the sensor.

Figure 5:
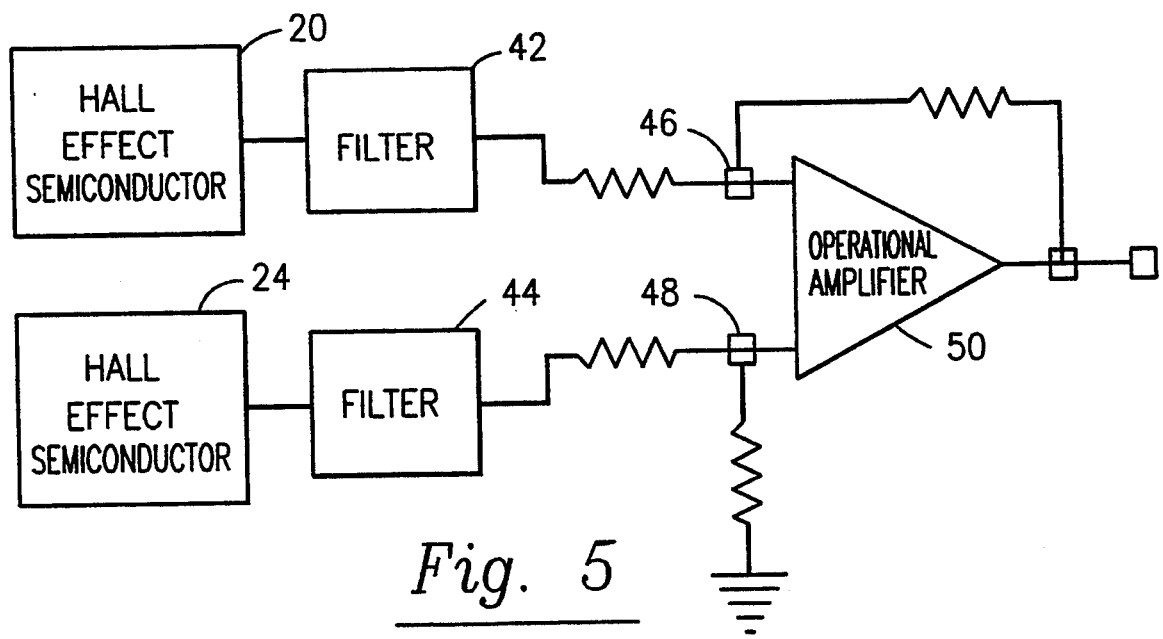
FIG. 5 is a schematic diagram partly in block diagram form of the subtraction circuit of the invention.

Referring now to FIG. 5, there is therein shown the operational amplifier of the crack detector sensor. The Hall Effects semiconductors 20 and 24 are each connected to a filter 42 and 44 respectively. Filters 42 and 44 are connected to input terminals 46 and 48 of an operational amplifier 50. Operational amplifier 50 is preferably a Texas Instrument TL 081 unit made by Texas Instruments, Inc. of Dallas, Tex.

The operational amplifier in the circuit in FIG. 5 is configured as a subtraction amplifier. The output of the amplifier is equal to the input at the positive terminal minus the input at the negative terminal. When two signals of the same amplitude appear coincidentally at the positive input and negative input, the output signal is zero. Any electromagnetic event external to the sensor will cause coincidental inputs at the operational amplifier, resulting in a null output at the amplifier. If a signal appears at either the positive input or the negative input, then the output signal will be the difference between the two inputs. A crack crossing the axis of the sensor element will cause one input to be greater than the other. This unbalanced input will cause a voltage to appear at the output of the amplifier. As the crack crosses the second detector, a voltage will appear at the amplifier that is opposite in polarity to the first detector. The output of the amplifier produces a signal that is a signature of a crack crossing the detector.

It should be understood that a similar operational amplifier circuit such as that shown in FIG. 5 will be connected to the pair of Hall Effect semiconductors 22 and 26 which are at a right angle with respect to Hall Effect semiconductors 20 and 24.

Figure 6:
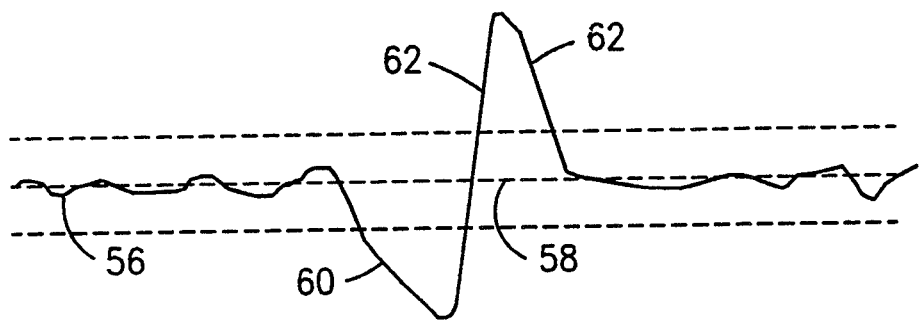
FIG. 6 is a graphical representation of the output signal of the subtraction circuit of FIG. 5.

The signal (FIG. 6) has a shape that identifies its source as a crack in the pipe wall. As explained previously, a non-zero voltage is present at the output of the circuit when a crack is in position under one of the semiconductors. As the sensor is moved so that the other semiconductor in the pair is positioned over the crack, another non-zero voltage will appear at the output of the circuit. This voltage will be equal in magnitude to the first, but opposite in polarity. If a pipe, which contains a crack in its wall, is rotated at a uniform speed under the crack detector sensor, a waveform such as shown in FIG. 6 will be generated. There is a small oscillation 56 about a centerline 58 in the wave as it goes from left to right in FIG. 6. This represents the normal background noise and residual magnetic field in the pipe wall. The voltage output of the circuit is essentially zero. As the crack 12 crosses into the sensing region of the first semiconductor 20, the output of the circuit becomes negative and the wave 60 moves sharply downward. The pipe continues to rotate and the crack moves under the second semiconductor 24. The circuit output wave 62 swings back through zero and becomes positive, with approximately equal amplitude. A computer can be programmed to recognize this pattern so that it can detect a crack in the pipe by looking at the voltage output of the circuit. After the crack 12 has passed out of the sensor range, the signal once again oscillates about zero.

In place of a computer, a simple galvanometer with a pointer set at zero and capable of detecting positive and negative voltage signals may be used. Also an oscilloscope can be connected to the output terminals of the operational amplifier.

Figure 7:
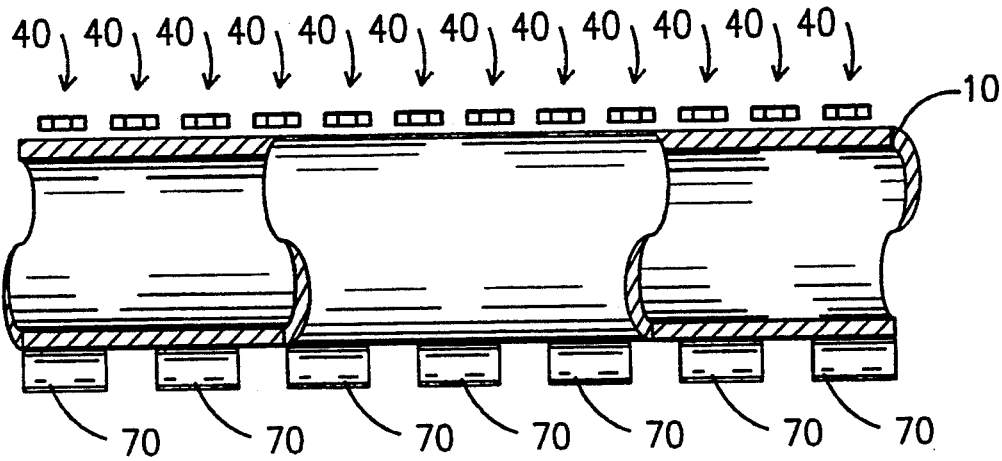
FIG. 7 is an elevational view partially in cross-section illustrating a series of fault detector sensors extending across the length of a magnetized object and being spaced an effective distance from said magnetized object.

FIG. 7 shows a series of flaw detectors 40 arranged longitudinally adjacent the upper surface of pipe 10 and a series of rollers 70 adapted to rotate pipe 10 beneath the series of flaw detectors 40, to simplify the drawings the means for rotating rollers 70 are not shown but are of conventional structure.

Referring now to FIG. 7, there is therein shown a magnetized object in the form of ferrous pipe 10 having a series of fault detector sensors 40 extending along the length of pipe 10. Sensors 40 are spaced an effective distance from pipe 10. A series of rollers 70 operated by means (not shown) causes pipe 10 to rotate under the row of sensors 40. Ferrous pipe 10 has been magnetized and given a remanent magnetic field in a manner previously described.

It should be understood that each sensor 40 shown in FIG. 7 will be connected to operational amplifiers such as that shown in FIG. 5 for each pair of Hall Effect semiconductors.

Before the crack detector sensor can operate, the pipe must have been magnetized. The magnetization is accomplished by inserting a wire 14 (FIG. 1) through the pipe along the central axis. A large current is passed through the wire. The pipe wall is left with a residual magnetic field when the current is stopped. Any cracks in the pipe wall will cause some of the magnetic flux to leak into the air. When the pipe is scanned with the sensor, the flux leakage, and therefore the crack, can be located.

In summary, a discontinuity in a pipe wall, either partially or completely through, will cause a magnetic field perturbation around the discontinuity. The purpose of the sensor in this invention is to locate the perturbed field if it exists. The detection of the field outside the pipe wall indicates the existence of a discontinuity in the pipe wall. The sensor is made from four Hall generators and five ferrite discs as previously described. The purpose of the ferrite discs in the sensor is to concentrate the magnetic flux around the Hall generators. The four Hall generators are placed 90 degrees apart so that they can respond to the field generated by the crack regardless of the orientation of the crack with respect to the axis of the pipe. At least one pair of sensors will respond to a completely axial or completely circumferential crack while both pair will respond to a crack between the extremes.

The presence of ferrite in the invention improves the sensitivity of the Hall generators. The magnitude of the flux density in the field is dependent on the value of the relative magnetic permeability of the objects in that field. The Hall generator is located between two pieces of material with a magnetic permeability 850 times the permeability of the air surrounding the sensor. The location of the Hall generator between the ferrite discs improves its ability to detect weak magnetic fields in the air.

While the present invention has been described with respect to specific embodiments thereof, it should be understood that the invention is not limited thereto as many modifications thereof may be made. It is therefore, contemplated to cover by the present application any and all such modifications as fall within the true spirit and scope of the appended claims.

We claim:

1. A sensor for detecting faults in a magnetized ferrous object comprising a first sensing element and a second sensing element in which said first sensing element comprises a centrally located ferrite disc and two Hall Effect semiconductors, said Hall Effect semiconductors being affixed to opposite sides of said ferrite disc and in which said second sensing element comprises a centrally located ferrite disc and two Hall Effect semiconductors being affixed to opposite sides of said ferrite disc, said ferrite disc of said first sensing element and of said second sensing element being common to each of said elements, said first sensing element and said second sensing element being positioned at a right angle to each other, said first sensing element and said second sensing element emitting output signals upon detection of magnetic flux.

2. A sensor for detecting faults in a magnetized ferrous object comprising a first sensing element and a second sensing element, in which said first sensing element comprises a centrally located ferrite disc and two Hall Effect semiconductors, said Hall Effect semiconductors being affixed to opposite sides of said ferrite disc and in which said second sensing element comprises a centrally located ferrite disc and two Hall Effect semiconductors being affixed to opposite sides of said ferrite disc, said ferrite disc of said first sensing element and said second sensing element being common to each of said elements, said first sensing element and said second sensing element being positioned at a right angle to each other, said first sensing element and second sensing element emitting output signals upon detection of magnetic flux, and means for detecting the output signals from said first sensing element and said second sensing element whereby said output signals may indicate a fault in said magnetized ferrous body.

3. A sensor for detecting faults in a magnetized ferrous body as recited in claim 1 in which said ferrite discs comprise a ferrous powder molded into a shape having at least one quadrilateral surface and being sintered to form a solid.

4. A sensor for detecting faults in a magnetized ferrous object as recited in claim 1 in which said Hall Effect semiconductors are oriented in a direction so that their major faces are perpendicular to the magnetic flux emanating from said magnetized object.

5. A sensor for detecting faults in a magnetized ferrous object as recited in claim 1 in which both of said Hall Effect semiconductors in said first sensing element are oriented facing the see direction with respect to each other, said Hall Effect semiconductors in said first sensing element being oriented to be at a right angle with respect to said Hall Effect semiconductors in said second sensing element.

6. A sensor for detecting faults in a magnetized ferrous object as recited in claim 2 in which said means for detecting the output signals from said first sensing element and said second sensing element is a subtraction electronic circuit.

7. A sensor for detecting faults in a magnetized ferrous object as recited in claim 1 in which said ferrous object is a ductile iron pipe.

8. A sensor for detecting faults in a magnetized ferrous object as recited in claim 1 in which said ferrous object is a hollow ductile iron pipe and said ductile iron pipe being magnetized to exhibit a magnetic field.

9. A device for detecting faults in a magnetized object comprising a row of sensors extending along the length of said magnetized object, each of said sensors being spaced an effective distance from a said magnetized object, each of said sensors comprising a first sensing element and a second sensing element in which said first sensing element comprises a centrally located ferrite disc and two Hall Effect semiconductors, said Hall Effect semiconductors being affixed to opposite sides of said ferrite disc and in which said second sensing element comprises a centrally located ferrite disc and two Hall Effect semiconductors being affixed to opposite sides of said ferrite disc, said ferrite disc of said first sensing element and of said second sensing element being common to each of said sensing elements, and said first sensing element and said second sensing element being positioned at a right angle to each other, said first sensing element and said second sensing element emitting output signals upon detection of magnetic flux.

10. A sensor for detecting faults in a magnetized ferrous object as recited in claim 1 in which said first sensing element has an additional pair of ferrite discs, one of said ferrite discs of said additional pair of ferrous discs being affixed to a side of one of said Hall Effect semiconductors opposite said centrally located ferrite disc and the other of said ferrite discs of said additional pair of ferrite discs being affixed to the side of the other of said Hall Effect semiconductors opposite said centrally located ferrite disc.

11. A sensor for detecting faults in a magnetized ferrous object as recited in claim 1 in which said second sensing element has an additional pair of ferrite discs, one of said ferrite discs of said additional pair of ferrous discs being affixed to a side of one of said Hall Effect semiconductors opposite said centrally located ferrite disc and the other of said ferrite discs of said additional pair of ferrite discs being affixed to the side of the other of said Hall Effect semiconductors opposite said centrally located ferrite disc.

* * * * *